(12) United States Patent
Dixit et al.

(10) Patent No.: US 11,590,151 B2
(45) Date of Patent: Feb. 28, 2023

(54) PHARMACEUTICAL PASTE FORMULATIONS FOR SITE SPECIFIC APPLICATION

(71) Applicant: USpharma Ltd., Miami Lakes, FL (US)

(72) Inventors: Manesh A Dixit, Miami Lakes, FL (US); Partha S Sen, Valsad (IN); Rahul Botkar, Maharashtra (IN); Ashim K Sarkar, Alipurduar (IN)

(73) Assignee: USPHARMA LTD, Miami Lakes, FL (US)

( * ) Notice: Subject to any disclaimer, the term of this patent is extended or adjusted under 35 U.S.C. 154(b) by 0 days.

(21) Appl. No.: 17/002,183

(22) Filed: Aug. 25, 2020

(65) Prior Publication Data

US 2021/0060045 A1  Mar. 4, 2021

Related U.S. Application Data

(60) Provisional application No. 62/893,952, filed on Aug. 30, 2019.

(51) Int. Cl.
| | |
|---|---|
| *A61K 31/7016* | (2006.01) |
| *A61K 9/06* | (2006.01) |
| *A61K 47/36* | (2006.01) |
| *A61K 47/26* | (2006.01) |
| *A61K 47/12* | (2006.01) |
| *A61K 47/02* | (2006.01) |
| *A61K 47/10* | (2017.01) |

(52) U.S. Cl.
CPC ............ *A61K 31/7016* (2013.01); *A61K 9/06* (2013.01); *A61K 47/02* (2013.01); *A61K 47/10* (2013.01); *A61K 47/12* (2013.01); *A61K 47/26* (2013.01); *A61K 47/36* (2013.01)

(58) Field of Classification Search
CPC .... A61P 1/00; A61K 7/20; A61K 9/00; A61Q 11/00
USPC .......................... 424/78.03, 422, 401; 514/12
See application file for complete search history.

(56) References Cited

U.S. PATENT DOCUMENTS

| | | | |
|---|---|---|---|
| 5,240,710 A * | 8/1993 | Bar-Shalom | A61K 8/735 424/422 |
| 5,444,054 A * | 8/1995 | Garleb | A23L 33/40 426/72 |
| 5,447,918 A | 9/1995 | McCullough | |
| 5,955,502 A * | 9/1999 | Hansen | A61K 9/1274 514/558 |
| 5,968,906 A | 10/1999 | Kashimura et al. | |
| 6,159,449 A * | 12/2000 | Winston | A61K 8/19 424/49 |
| 7,795,239 B2 | 9/2010 | McCullough | |
| 8,367,635 B2 | 2/2013 | McGrath | |
| 2014/0349927 A1 * | 11/2014 | Weinstock-Rosin | A61P 1/04 514/6.5 |

OTHER PUBLICATIONS

McElvanna et al., "Sucralfate paste: a new method of topical treatment for haemorrhatic radiation proctitis." Colorectal Disease vol. 16, Issue 4, Dec. 2013 (Year: 2013).*

* cited by examiner

*Primary Examiner* — Walter E Webb
(74) *Attorney, Agent, or Firm* — West Law Office LLC

(57) ABSTRACT

A pharmaceutical paste formulation containing an active ingredient, an API solubilizer, a cross-linking agent, a consistency improver, a rheology modifier, a humectant, and a liquid base.

4 Claims, 1 Drawing Sheet

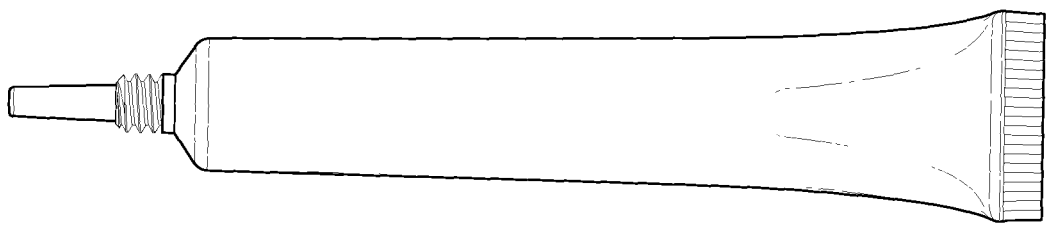

PHARMACEUTICAL PASTE FORMULATIONS FOR SITE SPECIFIC APPLICATION

RELATED APPLICATIONS

The present application claims the benefit of U.S. Provisional Patent Application Ser. No. 62/893,952, filed Aug. 30, 2019, entitled PHARMACEUTICAL PASTE FORMULATIONS FOR SITE SPECIFIC APPLICATION, which is hereby incorporated in its entirety by reference herein.

BACKGROUND

The present invention relates to improved pharmaceutical paste/gel formulations that are easily spreadable and can be applied using a wide range of devices for site specific application (e.g., single-and-multi-use squeezable tubes, syringes, etc.).

Generally, topical pharmaceutical formulations have localized action of an active agent/ingredient at the site of application with little-to-no systemic exposure, whereas transdermal pharmaceutical formulations deliver active agents/ingredients body-wide (systemically).

Recurrent aphthous stomatitis (commonly referred to as canker sores, hereinafter referred to as "RAS") is a common oral disorder affecting over half of the population of the United States where painful circular yellowish sores develop on the oral mucosa. RAS typically affects the softer parts of the mouth that move, such as the tongue, soft palate, cheeks, and lips. RAS is said to be "recurrent" because a sore usually reappears in the same or a new location after healing. In some cases, multiple ulcers are present, some of which may be healing while others are just starting to appear. There are three (3) main subtypes of RAS: (1) minor aphthous stomatitis; (2) major aphthous stomatitis; and (3) herpetiform aphthous stomatitis. Minor aphthous stomatitis is the most common subtype, constituting more than eighty (80) percent of RAS cases, and is generally characterized by small (i.e., less than one (1) centimeter in diameter) sores that heal in approximately one (1) week and do not typically result in the formation of scar tissue. Major aphthous stomatitis is the second most common form of RAS, constituting approximately fifteen (15) percent of RAS cases, and is generally characterized by slightly larger (i.e., greater than one (1) centimeter in diameter) sores that take longer to heal (i.e., two (2) or more weeks) and are extremely painful and often result in the formation of scar tissue. Herpetiform aphthous stomatitis is the least common subtype of RAS, occurring in less than five (5) percent of RAS cases, and is generally characterized by clusters of very small ulcers (i.e., less than one (1) millimeter) that typically heal in approximately one (1) week.

The treatment of RAS with sucralfate is generally known. For instance, ProThelial™ "is polymerized sucralfate malate paste that forms a protective layer over the oral mucosa by adhering to the mucosal surface" marketed by Mueller Medical International LLC. ProThelial™ is a thick gel packaged in a wide mouth bottle. ProThelial™ users are instructed to remove the product from the bottle using a spoon and to apply the product to the affected area using the "tongue to apply paste throughout the mouth (as if using tongue to remove peanut butter from teeth)." Known sucralfate formulations for treating RAS require broad range application to the entire mouth by swishing/gargling and tend to dry-up on storage due to high solid content and sucralfate's high water absorbing capacity.

Thus, there is a need for sucralfate formulations that can be applied to ulcers on a site specific basis using an applicator, such as a squeezable tube, and that will not dry and harden in storage.

SUMMARY OF THE INVENTION

The following brief summary is provided to indicate the nature of the subject matter disclosed herein. While certain aspects of the present invention are described below, the summary is not intended to limit the scope of the present invention.

Pharmaceutical paste/gel formulations according to the present invention provide several advantages over the prior art. For instance, certain embodiments of the present invention relate to soothing mucoadhesive pharmaceutical gels for treating RAS that: can be provided to patients in site specific applicators (such as a squeezable tube), which enable direct application on the lesions; spread easily and adhere better (relative to the prior art) to the affected area; will not exhibit increased viscosity over a longer shelf-life due to moisture loss and/or reactions between excipients; provide reduced irritability and improved taste; do not require the patient or physician to perform additional processing steps prior to application; and/or are free of preservatives. It should be understood that the present invention is not limited to the foregoing advantages and that other technical advantages may become readily apparent to one of ordinary skill in the art after review of the description.

Pharmaceutical paste/gel formulations according to certain aspects of the present invention have Bingham plastic rheology, which means the inventive formulations behave as viscoplastics (i.e., behaves as a rigid body at low stresses but flows as a viscous fluid at high stress). This rheological property enables users to accurately deliver the pharmaceutical gel directly on the ulcerative lesions using a site specific applicator (such as a squeezable tube having an applicator tip). Such pharmaceutical gel formulations can be described as a congealed base having a high proportion of solids in a finely dispersed form.

Pharmaceutical paste/gel formulations according to the present invention retain moisture; for instance, by inclusion of one or more humectants and/or rheology modifiers. Moisture retention facilitates fluidity by, among other things, reducing resistance to movement of solid particles in the dispersed phase. Known sucralfate products do not retain adequate moisture, and solids in the dispersed phase tend to aggregate, which contributes to their higher viscosity and limited application.

Certain aspects of the present invention relate to a medical device consisting of a ready-to-use topical pharmaceutical formulation contained within functional packaging designed to enable the user to apply the formulation directly on treatment location.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the present invention will be apparent from the following detailed description of the embodiments and the accompanying drawing FIGURES.

BRIEF DESCRIPTION OF THE DRAWING FIGURES

Preferred embodiments of the invention are described in detail below with reference to the attached FIGURES, wherein:

FIG. 1 is a side perspective view of a medical device containing a pharmaceutical paste/gel formulation manufactured in accordance with certain embodiments of the present invention.

The FIGURES do not limit the present invention to the specific embodiments disclosed and described herein. The emphasis instead being placed upon clearly illustrating the principles of a preferred embodiment.

DETAILED DESCRIPTION OF THE PREFERRED EMBODIMENTS

The present invention is susceptible of embodiment in many different forms. While the FIGURES show, and the specification describes, certain preferred embodiments of the invention, it is to be understood that such disclosure is by way of example only. There is no intent to limit the principles of the present invention to the particular disclosed embodiments.

Certain aspects of the present invention are directed to pharmaceutical paste/gel formulations. In certain embodiments of the present invention, pharmaceutical paste/gel formulations preferably include one or more: active pharmaceutical ingredients; cros slinking agents; rheology modifiers; liquid bases; taste modifiers; and other excipients. However, those having ordinary skill in the art will understand that other formulations are within the scope of the present invention.

In certain embodiments of the present invention, the active pharmaceutical ingredient is sucralfate. Sucralfate is a disaccharide polysulfate-aluminum compound, more specifically referred to as alpha-D-glucopyranoside, beta-D-fructofuranosyl, catkins (hydrogen sulfate), aluminum complex having the structure shown below:

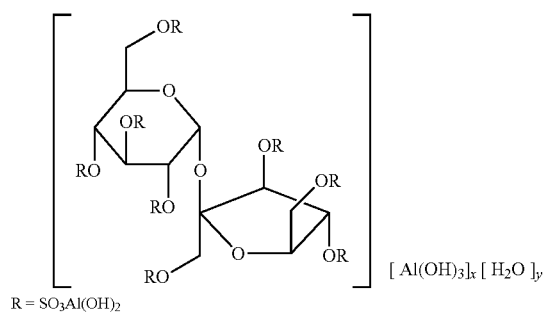

R = SO$_3$Al(OH)$_2$

Sucralfate has been used to manage lesions in the oral cavity (e.g., aphthous ulcers, stomatitis, etc.). Sucralfate adheres to the mucosal surface and forms a protective layer over the oral mucosa to reduce irritation and pain caused by lesions in the oral cavity. Sucralfate is an oral "anti-ulcer" and gastrointestinal drug, which has been used to treat or prevent the recurrence of ulcers by protecting stomach or duodenal lining from the effects of various irritants (e.g., alcohol, acetylsalicylic acid, hydrochloric acid, sodium hydroxide, sodium taurocholate, etc.). Sucralfate has also been considered as first-line drug therapy in the management of heartburn in pregnancy. Sucralfate is used as a topical drug for the healing of several types of epithelial wounds such as ulcers, inflammatory dermatitis, mucositis, and burn wounds.

In certain embodiments of the present invention, the pharmaceutical paste/gel formulation includes one or more API solubilizers. For instance, sucralfate is practically insoluble in water, so an API solubilizer may be incorporated in the formulation to decrease the pH of water and to solubilize sucralfate, which facilitates the polymerization of sucralfate. A wide range of API solubilizers can be used in the pharmaceutical paste/gel formulations of the present invention, including, but not limited to, one or more API solubilizers selected from the group consisting of citric acid, lactic acid, malic acid, and tartaric acid. It should be understood that certain embodiments of the present invention are not limited to the use of the foregoing API solubilizers. Furthermore, other ingredients may be used that function as API solubilizers without departing from the spirit of the present invention.

In certain embodiments of the present invention, the pharmaceutical paste/gel formulation includes one or more API solubilizers at a concentration ranging, preferably, from about one-thousandth of one percent weight-by-weight (0.001% w/w) to about fifteen percent weight-by-weight (15% w/w). More preferably, the pharmaceutical paste/gel formulation includes one or more API solubilizers at a concentration ranging from about five one-hundredths of one percent weight-by-weight (0.05% w/w) to about ten percent weight-by-weight (10% w/w).

In certain embodiments of the present invention, preferred API solubilizers improve the solubility of the active ingredient in water. In certain embodiments of the present invention, malic acid is used to improve the solubility of sucralfate in water, with the compositional ratio of malic acid to sucralfate in at least one preferred embodiment being approximately one-to-two (1:2). In certain embodiments of the present invention, malic acid also helps facilitate water retention in the pharmaceutical paste/gel throughout its shelf life. It should be understood that certain embodiments of the present invention are not limited to the use of malic acid as an API solubilizer. Furthermore, other ingredients may be used without departing from the spirit of the present invention.

In certain embodiments of the present invention, the pharmaceutical paste/gel formulation includes one or more rheology modifiers. Rheology modifiers facilitate manufacture of a pharmaceutical paste/gel that is soft, spreadable, and will stay hydrated for longer periods of time, which enables packaging of the inventive pharmaceutical paste/gels in site specific applicators. A wide range of rheology modifiers can be used in the pharmaceutical paste/gel formulations of the present invention, including, but not limited to, one or more rheology modifiers selected from the group consisting of: carboxymethyl cellulose; cellulose derivatives; ethyl cellulose; hydroxypropyl cellulose; hydroxypropyl methylcellulose; methylcellulose;
microcrystalline cellulose; natural polysaccharides such as chitosan, pectin, guar gum, etc.; polyvinyl alcohol; povidone; propyl cellulose; sodium carboxymethyl cellulose; and xanthan gum. It should be understood that certain embodiments of the present invention are not limited to the use of the foregoing rheology modifiers. Furthermore, other ingredients that function as rheology modifiers may be used without departing from the spirit of the present invention.

In certain embodiments of the present invention, the pharmaceutical paste/gel formulation includes one or more rheology modifiers at a concentration ranging, preferably, from about five one-hundredths of one percent weight-by-weight (0.05% w/w) to about thirty percent weight-by-weight (30% w/w). More preferably, the pharmaceutical paste/gel formulation includes one or more rheology modifiers at a concentration ranging from about one percent weight-by-weight (1% w/w) to about twenty-five percent weight-by-weight (25% w/w).

Preferred rheology modifiers according to certain embodiments of the present invention are nontoxic and compatible with other pharmaceutical ingredients. Furthermore, preferred rheology modifiers enable certain preferred characteristic properties of pharmaceutical paste/gel formulations of the present invention; more particularly, preferred rheology modifiers: provide consistency to the formulation; provide increased viscosity in low concentrations; exhibit good stability and viscosity properties over a wide range of pH levels and temperatures; maintain the preferred texture properties of the formulation; and maintain thickening and stabilizing properties during long-term storage at elevated temperatures. One such preferred rheology modifier according to certain embodiments of the present invention is xanthan gum. Xanthan gum is a hydrophilic polymer. Xanthan gum is nontoxic and is compatible with a wide range of pharmaceutical ingredients. Xanthan gum shows high viscosity at low concentrations, provides consistency to the pharmaceutical paste/gel formulation, and helps maintain preferred textural properties of the inventive paste/gel formulations. Aqueous solutions of xanthan gum are stable over a wide range of pH levels (i.e., pH levels ranging from about three (3) to about twelve (12)). Xanthan gum remains stable in both acidic as well as in alkaline conditions due to its rigid structure and resistance to changes in pH. Xanthan gum gels show pseudo plastic behavior, the shear thinning directly proportional to the shear rate; viscosity turns to normal immediately on release of shear stress. It should be understood that certain embodiments of the present invention are not limited to the use of xanthan gum as a rheology modifier. Furthermore, other ingredients may be used as rheology modifiers without departing from the spirit of the present invention.

In certain embodiments of the present invention, pharmaceutical paste/gel formulations include one or more humectants. A wide range of humectants can be used in the pharmaceutical paste/gel formulations of the present invention, including, but not limited to, one or more humectants selected from the group consisting of propylene glycol, polyethylene glycol, glycerin, sorbitol, hexylene glycol, and butylene glycol. It should be understood that certain embodiments of the present invention are not limited to the use of a specific humectant. Furthermore, other ingredients that function as humectants may be used without departing from the spirit of the present invention.

Preferred humectants according to certain embodiments of the present invention facilitate water retention in the inventive pharmaceutical paste/gels, which enables pharmaceutical paste/gels to be packaged in site specific applicators by preventing drying and hardening of the pharmaceutical paste/gel within such applicators. One such preferred humectant according to certain embodiments of the present invention is propylene glycol. Propylene glycol facilitates water retention in the pharmaceutical paste/gel formulation over a sufficient period of time, which enables such pharmaceutical paste/gels to be packaged in site specific applicators. Furthermore, propylene glycol hydrates the mucosa and may help reduce irritation associated with lesions in the oral cavity, and can also improve palatability given its sweet taste. It should be understood that certain embodiments of the present invention are not limited to the use of propylene glycol as a humectant. Furthermore, other ingredients may be used without departing from the spirit of the present invention.

In certain embodiments of the present invention, the pharmaceutical paste/gel formulation includes one or more humectants at a concentration ranging, preferably, from about five one-hundredths of one percent weight-by-weight (0.05% w/w) to about thirty percent weight-by-weight (30% w/w). More preferably, the pharmaceutical paste/gel formulation includes one or more humectants at a concentration ranging from about one percent weight-by-weight (1% w/w) to about twenty-five percent weight-by-weight (25% w/w).

In certain embodiments of the present invention, one or more crosslinking agents are used to facilitate polymerization of the active ingredient in the presence of organic acids, acting as a cross-linker for the active ingredient and the acid. A wide range of crosslinking agents can be used in the pharmaceutical paste/gel formulations of the present invention, including, but not limited to, one or more crosslinking agents selected from the group consisting of bicarbonates, calcium carbonate, magnesium carbonate, and magnesium oxide. It should be understood that certain embodiments of the present invention are not limited to the use of a specific crosslinking agent. Furthermore, other ingredients that function as a crosslinking agent may be used without departing from the spirit of the present invention.

In certain embodiments of the present invention, the pharmaceutical paste/gel formulation includes one or more crosslinking agents at a concentration ranging, preferably, from about one-thousandth of one percent weight-by-weight (0.001% w/w) to about ten percent weight-by-weight (10% w/w). More preferably, the pharmaceutical paste/gel formulation includes one or more crosslinking agents at a concentration ranging from about five one-hundredths of one percent weight-by-weight (0.05% w/w) to about five percent weight-by-weight (5% w/w).

In certain embodiments of the present invention, the inventive pharmaceutical paste/gels have a pH value of approximately five (5) to about seven (7). At pH levels of less than about four (4), sucralfate undergoes extensive polymerization and becomes a sticky, viscid gel. At pH levels of greater than about four (4), a cross-linking agent facilitates the desired characteristics of spreadability, adhesion, and mucosal affinity. In certain embodiments of the present invention, calcium carbonate is a preferred crosslinking agent based on the chelation formation between the calcium ions (Ca2+) of calcium carbonate and the aluminum ions (Al3+) of the sucralfate complex. In certain embodiments of the present invention, calcium carbonate also acts as buffering agent; maintaining the pH level of sucralfate paste/gel at range about five (5) to about seven (7), which is approximately the same as the pH of saliva. In certain embodiments of the present invention, calcium carbonate is used as a crosslinking agent at a concentration ranging, preferably, from about one percent weight-by-weight (1% w/w) to about five percent weight-by-weight (5% w/w). It should be understood that certain embodiments of the present invention are not limited to the use of calcium carbonate as a crosslinking agent. Furthermore, other ingredients may be used without departing from the spirit of the present invention.

In certain embodiments of the present invention, where the pharmaceutical paste/gel formulation includes sucralfate and malic acid (as an API solubilizer), it may be preferable to include malic acid and calcium carbonate in a specific ratio of one-to-two (1:2) to avoid phase separation during processing stage, which can cause sucralfate to precipitate-out of the final composition. It should be understood that certain embodiments of the present invention are not limited to the use of calcium carbonate as a cros slinking agent and/or malic acid as an API solubilizer. Furthermore, other ingredients may be used without departing from the spirit of the present invention.

In certain embodiments of the present invention, the pharmaceutical paste/gel formulation includes one or more consistency improvers. Consistency improvers reduce lumping of the pharmaceutical paste/gel formulation and improve the paste/gel's overall consistency. In certain embodiments of the present invention, calcium sulphate dihydrate is used as a consistency improver to reduce lumping of sucralfate and calcium carbonate and improve the pharmaceutical paste/gel's consistency. It should be understood that certain embodiments of the present invention are not limited to the use of a consistency improver. Furthermore, other ingredients that function as a consistency improver may be used without departing from the spirit of the present invention.

In certain embodiments of the present invention, the pharmaceutical paste/gel formulation includes one or more consistency improvers at a concentration ranging, preferably, from about one-thousandth of one percent weight-by-weight (0.001% w/w) to about ten percent weight-by-weight (10% w/w). More preferably, the pharmaceutical paste/gel formulation includes one or more consistency improvers at a concentration ranging from about one-hundredth of one percent weight-by-weight (0.01% w/w) to about one percent weight-by-weight (1% w/w).

In certain embodiments of the present invention, the pharmaceutical paste/gel formulation includes one or more stabilizers. Stabilizers are used to help the active pharmaceutical ingredient maintain desirable properties of the pharmaceutical product until the it is used by the patient; for example, stabilizers can be used to control degradation of the active ingredient. Suitable stabilizers include, but are not limited to, organic acids and inorganic acids. In certain embodiments of the present invention, preferred stabilizers include ethylenediaminetetraacetic acid (hereinafter referred to as "EDTA") and/or sodium edetate; however, it should be understood that certain embodiments of the present invention are not limited to the use of a stabilizer. Furthermore, other ingredients that function as a stabilizer may be used without departing from the spirit of the present invention.

In certain embodiments of the present invention, the pharmaceutical paste/gel formulation includes one or more liquid bases, which act a vehicle for other ingredients. In certain embodiments of the present invention, the liquid base will, preferably, serve as both a vehicle and a hydrating agent. In certain embodiments of the present invention, the polymerization of sucralfate with malic acid and calcium carbonate takes place in presence of purified water (as the liquid base). It should be understood that certain embodiments of the present invention are not limited to the use of a specific liquid base. Furthermore, other ingredients that function as a vehicle may be used without departing from the spirit of the present invention.

In certain embodiments of the present invention, the pharmaceutical paste/gel formulation includes a liquid base at a concentration ranging, preferably, from about one percent weight-by-weight (1% w/w) to about ninety-five percent weight-by-weight (95% w/w). More preferably, the pharmaceutical paste/gel formulation includes a liquid base at a concentration ranging from about ten percent weight-by-weight (10% w/w) to about ninety percent weight-by-weight (90% w/w).

In certain embodiments of the present invention, the pharmaceutical paste/gel formulation includes one or more taste modifiers improve the palatability of the formulation. Taste modifiers may include one or more sweetening agents, flavor enhancers, and/or flavoring agents. In certain preferred embodiments of the present invention, the pharmaceutical paste/gel formulation includes one or more taste modifiers selected from the group consisting of stevia, aspartame, sucralose, neotame, acesulfame potassium, saccharin, and advantame; however, it should be understood that the present invention is not limited to the use of the foregoing taste modifiers. Furthermore, other ingredients that function as a taste modifier may be used without departing from the spirit of the present invention.

In certain embodiments of the present invention, the pharmaceutical paste/gel formulation includes one or more taste modifiers at a concentration ranging, preferably, from about five one-thousandths of one percent weight-by-weight (0.005% w/w) to about ten percent weight-by-weight (10% w/w). More preferably, the pharmaceutical paste/gel formulation includes one or more taste modifiers at a concentration ranging from about one-hundredth of one percent weight-by-weight (0.01% w/w) to about five percent weight-by-weight (5% w/w).

Pharmaceutical paste/gels manufactured in accordance with preferred embodiments of the present invention are capable of being packaged in a squeezable tube having a site specific applicator nozzle. For instance, pharmaceutical paste/gels manufactured in accordance with preferred embodiments of the present invention are capable of being packaged in a primary packaging tube similar to that described in Table 1 below and shown in FIG. 1.

TABLE 1

| Parameter | Description |
| --- | --- |
| Package Type | Laminated tube |
| Length with shoulder (mm) | 100 |
| Length without shoulder (mm) | 83.5 |
| Tube diameter (mm) | 16 |
| Inner Nozzle Diameter (mm) | 0.61 |
| Outer Nozzle Diameter (mm) | 3.51 |
| Nozzle length (mm) | 14.25 |
| Tube wall thickness (mm) | 0.18 |
| Total Thickness ($\mu$) | 175 ± 10% |
| Total GSM | 186.96 ± 10% |
| Shelf Life | 2 years in tube form or without filled product |
| Barrier layer | Aluminum Foil Thickness ($\mu$) 9 |
| TIE layer | EAA Thickness ($\mu$) 20.5 |
| Outer white film | Polyethylene Thickness ($\mu$) 75 |
| Joint type | Butt joints (no overlapping) with heat resistant adhesive tapes on both sides. |
| Manufacturer | Essel Propack Ltd. |

EXAMPLES

The following Examples set forth preferred therapeutic agents and methods in accordance with the invention, but it is to be understood that these Examples are given by way of illustration only, and nothing therein should be taken as a limitation upon the overall scope of the invention.

Ingredients corresponding to Example 1 (10% sucralfate pharmaceutical paste/gel) are tabulated in Table 2, with the amount of each ingredient given in respective percent weight-by-weight (% w/w). In Example 1, the active ingredient is sucralfate. In Example 1, the active strength of sucralfate is about ten percent (10%).

TABLE 2

| Ingredient | Type | % w/w |
| --- | --- | --- |
| Sucralfate | Active Ingredient | 10.000 |
| Malic acid | API Solubilizer | 5.000 |
| Calcium carbonate | Crosslinking Agent | 1.000 |
| Polyvinylpyrrolidone K-30 | Rheology Modifier | 3.820 |
| Polyvinylpyrrolidone K-90 | Rheology Modifier | 3.820 |
| Calcium sulfate dihydrate | Consistency Improver | 0.100 |
| EDTA | Stabilizer | 0.020 |
| Sucralose | Taste Modifier | 0.020 |
| Propylene glycol | Humectant | 7.000 |
| Purified water | Liquid Base | 69.220 |
| TOTAL | | 100.00 |

Procedure—Example 1

Step 1: triturate the batch quantity of malic acid to fine powder by using mortar pestle.

Step 2: add the batch quantities of calcium carbonate and sucralfate, simultaneously, to the triturated malic acid of Step 1 under continuous trituration until a uniform mixture is formed.

Step 3: add approximately twelve percent (12%) of the batch quantity of purified water to the mixture of Step 2 under continuous trituration, mix well until thick, sticky gel forms, and allow the mixture to soak for approximately thirty (30) minutes.

Step 4: add approximately forty percent (40%) of the batch quantity of purified water to a container, and add the batch quantities of polyvinylpyrrolidone K-30, polyvinylpyrrolidone K-90 to the purified water under continuous stirring at about eight hundred (800) rpm for approximately about ten (10) minutes.

Step 5: add the batch quantities of EDTA, calcium sulfate dihydrate, and sucralose to the mixture of Step 4 under continuous stirring at about eight hundred (800) rpm for approximately fifteen (15) minutes.

Step 6: add and mix the paste of Step 3 to the mixture of Step 5 under continuous high speed stirring at about one thousand five hundred (1500) rpm for approximately one hundred twenty (120) minutes to form a uniform mixture.

Step 7: add and mix the batch quantity of propylene glycol to the mixture of Step 6 under continuous high speed stirring at about one thousand five hundred (1500) rpm.

Step 8: add the remaining batch quantity of purified water to the mixture of Step 7 and stir continuously.

Step 9: let the mixture of Step 8 set for approximately twelve (12) hours—a paste/gel should begin to form after approximately five (5) to six (6) hours.

Table 3: Characterization of the pharmaceutical paste/gel formed in accordance with Example 1:

TABLE 3

| Appearance | Opaque |
| --- | --- |
| Texture | Smooth |
| Color | White |
| Assay (percentage) | 93.4 |

Ingredients corresponding to Example 2 (10% sucralfate pharmaceutical paste/gel) are tabulated in Table 4, with the amount of each ingredient given in respective percent weight-by-weight (% w/w). In Example 2, the active ingredient is sucralfate. In Example 2, the active strength of sucralfate is about ten percent (10%).

TABLE 4

| Ingredient | Type | % w/w |
| --- | --- | --- |
| Sucralfate | Active Ingredient | 10.000 |
| Malic acid | API Solubilizer | 5.000 |
| Calcium carbonate | Cross Linking Agent | 2.500 |
| Xanthan gum | Rheology Modifier | 0.500 |
| Calcium sulfate dihydrate | Consistency Improver | 0.100 |
| Sucralose | Taste Modifier | 0.020 |
| Propylene glycol | Humectant | 7.000 |
| Purified water | Liquid Base | 74.880 |
| TOTAL | | 100.00 |

Procedure—Example 2

Step 1: add approximately sixty-five percent (65%) of the batch quantity of purified water to a vessel and add and dissolve the batch quantity of malic acid under continuous stirring at about one thousand two hundred (1200) rpm for approximately ten (10) minutes.

Step 2: add the batch quantity sucralfate to the mixture of Step 1 under continuous stirring at about one thousand eight hundred (1800) rpm for approximately thirty (30) minutes (a uniform dispersion should be observed).

Step 3: add the batch quantity of calcium carbonate to the mixture of Step 2 under continuous stirring until a uniform mixture is formed (approximately about forty (40) minutes).

Step 4: add the batch quantities of calcium sulfate dihydrate and sucralose to the mixture of Step 3 under continuous homogenization at about two thousand five hundred (2500) rpm, until a uniform dispersion is formed.

Step 5: slowly add and dissolve the batch quantity of xanthan gum to the dispersion of Step 4 under continuous homogenization at about two thousand five hundred (2500) rpm.

Step 6: add and mix the batch quantity of propylene glycol to the mixture of Step 5 under continuous stirring at about one thousand five hundred (1500) rpm for approximately ten (10) minutes.

Table 5: Characterization of the pharmaceutical paste/gel formed in accordance with Example 2.

TABLE 5

| Sample | Appearance | Texture | Color |
| --- | --- | --- | --- |
| EX 2 | Opaque | Smooth | White |
| EX 2[1] | Opaque | Smooth | White |
| EX 2[2] | Opaque | Smooth | White |
| EX 2[3] | Opaque | Smooth | White |

[1] one-month stability at 40° C. and 75% relative humidity ("RH").
[2] three-month stability 40° C. and 75% RH.
[3] three-month stability 25° C. and 60% RH.

Table 6: pH value and water content of the pharmaceutical paste/gel formed in accordance with Example 2.

TABLE 6

| Sample | pH | Water Content (percentage) |
|---|---|---|
| EX 2 | 6.38 | 69.1908 |
| EX 2[1] | 5.65 | 59.6283 |
| EX 2[2] | 5.86 | 60.7621 |
| EX 2[3] | 5.75 | 62.0086 |

[1]one-month stability at 40° C. and 75% relative humidity ("RH").
[2]three-month stability 40° C. and 75% RH.
[3]three-month stability 25° C. and 60% RH.

Analysis results concerning the chemical characterization and acid neutralizing capacity (performed as given in United States Pharmacopeia (USP) general chapter <301> Acid-neutralizing capacity) of the pharmaceutical paste/gel formed in accordance with Example 2 are tabulated in Table 7.

TABLE 7

| Sample | Assay (percentage) | Acid Neutralizing Capacity |
|---|---|---|
| EX 2 | 106.2 | 13.51 |
| EX 2[1] | 100.3 | 13.21 |
| EX 2[2] | 99.2 | 13.03 |
| EX 2[3] | 104.1 | 13.2 |

[1]one-month stability at 40° C. and 75% relative humidity ("RH").
[2]three-month stability 40° C. and 75% RH.
[3]three-month stability 25° C. and 60% RH.

The results of a microbial enumeration analysis (conducted in accordance with USP general chapter <61> microbiological examination of nonsterile products: microbial enumeration tests) of the pharmaceutical paste/gel formed in accordance with Example 2 are tabulated in Table 8.

TABLE 8

| Test | Result | Specification |
|---|---|---|
| Total aerobic microbial count | <10 cfu/g | NMT $10^2$ cfu/g |
| Total combined yeast and mold count | <10 cfu/g | NMT $10^1$ cfu/g |
| Escherichia coli | Absent/g | Absent/g |
| Pseudomonas aeruginosa | Absent/g | Absent/g |
| Staphylococcus aureus | Absent/g | Absent/g |
| Salmonella species | Absent/10 g | Absent/10 g |

Modifications, additions, and/or omissions may be made to the compositions, methods, and steps described herein without departing from the scope of the disclosure. For example, the ingredients of the composition and method for manufacture may be integrated or separated. Moreover, the method for manufacture disclosed herein may be prepared by more, fewer, or other ingredients and the methods described may include more, fewer, or other steps. Additionally, steps may be performed in any suitable order.

The preferred forms of the invention described above are to be used as illustration only, and should not be utilized in a limiting sense in interpreting the scope of the present invention. Obvious modifications to the exemplary embodiments, as hereinabove set forth, could be readily made by those skilled in the art without departing from the spirit of the present invention.

The inventors hereby state their intent to rely on the Doctrine of Equivalents to determine and assess the reasonably fair scope of the present invention as pertains to any apparatus not materially departing from but outside the literal scope of the invention as set forth in the following claims.

What is claimed is:

1. A pharmaceutical formulation comprising:
   sucralfate, as an active pharmaceutical ingredient, in a concentration ranging from about 8% w/w to about 12% w/w;
   malic acid, as an API solubilizer, in a concentration ranging from about 4.8% w/w to about 5.2% w/w;
   calcium carbonate, as a cross-linking agent, in a concentration ranging from about 2.4% w/w to about 2.6% w/w;
   calcium sulfate dihydrate, as a consistency improver, in a concentration ranging from about 0.05% w/w to about 1.5% w/w;
   xanthan gum, as a rheology modifier, in a concentration ranging from about 0.1% w/w to about 1.0% w/w; and
   propylene glycol, as a humectant, in a concentration ranging from about 2% w/w to about 10% w/w,
   wherein said pharmaceutical formulation is capable of being:
   packaged in a squeezable tube fitted with a site-specific applicator having an inner nozzle diameter of 0.61 mm;
   stored in said squeezable tube for a period of time of 2-years; and
   expelled from the squeezable tube through the site-specific applicator throughout said period of time.

2. The pharmaceutical formulation as claimed in claim 1, wherein said pharmaceutical formulation has a water content ranging from an about 56% w/w to about 85% w/w.

3. The pharmaceutical formulation as claimed in claim 1, further comprising sucralose.

4. The pharmaceutical formulation as claimed in claim 3, said sucralose being present in a concentration ranging from about one-hundredth of one percent weight-by-weight (0.01% w/w) to about one percent weight-by-weight (1% w/w).

* * * * *